United States Patent
Viron et al.

(10) Patent No.: US 6,447,782 B1
(45) Date of Patent: Sep. 10, 2002

(54) LIPID EXTRACT OF THE SKELETONEMA ALGAE

(75) Inventors: Cécile Viron, Orleans; Valérie Krzych, Les Bordes; Isabelle Renimel, Trainou; Patrice Andre, Neuville aux Bois, all of (FR)

(73) Assignee: Parfums Christian Dior, Paris (FR)

( * ) Notice: Subject to any disclaimer, the term of this patent is extended or adjusted under 35 U.S.C. 154(b) by 0 days.

(21) Appl. No.: 09/786,723

(22) PCT Filed: Sep. 9, 1999

(86) PCT No.: PCT/FR99/02144
§ 371 (c)(1),
(2), (4) Date: Mar. 8, 2001

(87) PCT Pub. No.: WO00/13660
PCT Pub. Date: Mar. 16, 2000

(30) Foreign Application Priority Data

Sep. 9, 1998 (FR) ............................................. 98 11241

(51) Int. Cl.[7] ................................................ A61K 35/80
(52) U.S. Cl. ................ 424/195.17; 424/780; 424/78.02; 424/78.05; 424/401; 424/400; 424/78.03
(58) Field of Search .............................. 424/401, 78.02, 424/78.05, 780, 195.17

(56) References Cited

U.S. PATENT DOCUMENTS

| | | | | |
|---|---|---|---|---|
| 4,810,424 | A | * | 3/1989 | Gerwick et al. |
| 5,310,554 | A | * | 5/1994 | Haigh |
| 5,767,095 | A | * | 6/1998 | Winget |

FOREIGN PATENT DOCUMENTS

| | | | |
|---|---|---|---|
| EP | 52777 A | * | 6/1982 |
| FR | 2 657 012 | | 7/1991 |
| FR | 2 683 720 | | 5/1993 |
| JP | 409176022 A | * | 7/1997 |
| WO | 94/24984 | | 11/1994 |
| WO | 94/28913 | | 12/1994 |

OTHER PUBLICATIONS

Brockerhoff et al., "Fatty Acid Distribution in Lipids of Marine Plankton", J Fisheries Res Board Can, 1964, 21(6), p. 1379–1384.*
Berge et al., "Antiproliferative Effects of an Organic Extract from the Marine Diatom Skeletonema costatum (Grev) Cleve. Against a Non–small Cell Bronchopulmonary Carcinoma Line (NSCLC–N6)", Anticancer Res, 1997, 17:2115–2120.*
Balaban et al., "Extraction of algae lipids with supercritical carbon dioxide", Engineering and Food, vol. 3:Advanced processes, 1990, Elsevier Applied Science Publishers, London, p. 166–182.*
<<http://home.planet.nl/~skok/universal/techniques/hplc/eluotropic_series_extended.html>>.*
Polak, J.T., et al. "Supercritical carbon dioxide extraction of lipids from algae", STN, abstract XP–002125164.
Servel M., et al. "Fatty acid composition of some marine microalgae", STN, abstract XP–002125163.

* cited by examiner

Primary Examiner—Leon B. Lankford, Jr.
Assistant Examiner—Ruth A. Davis
(74) Attorney, Agent, or Firm—Nath & Associates PLLC; Gary M. Nath; Todd L. Juneau

(57) ABSTRACT

The invention relates to a novel lipid extract of the algae Skeletonema, especially the algae *Skeletonema costatum*.

In particular, this extract is a total lipid extract of said algae. It can be obtained by extracting the algae Skeletonema in an organic solvent which has a polarity index p' of less than about 5.4, preferably of between 2 and 4.5 and particularly preferably of between 4.2 and 4.4, and which is acceptable in the cosmetic or pharmaceutical industry.

This extract can be used as an active principle for the manufacture of a cosmetic or pharmaceutical composition particularly for producing a slimming, anti-cellulite, skin anti-ageing or sensitive skin treatment.

24 Claims, No Drawings

LIPID EXTRACT OF THE SKELETONEMA ALGAE

The invention relates to a novel lipid extract of the algae Skeletonema, to a process for its preparation and to its use in the fields of cosmetics and pharmaceutics, especially dermatology.

This algae belongs to the genus Skeletonema and is in particular the algae *Skeletonema tropicum, Skeletonema menzelii, Skeletonema potamos, Skeletonema subsalsum, Skeletonema pseudocostatum* or *Skeletonema costatum*.

The invention relates more precisely to uses of a lipid extract of this algae as a cosmetic agent.

The algae Skeletonema, in particular the algae *Skeletonema tropicum, Skeletonema menzelii, Skeletonema potamos, Skeletonema subsalsum, Skeletonema pseudocostatum* or *Skeletonema costatum* (called SKC in the remainder of -the document), is a well-known single-cell algae of the phylum Chlorophytes, the branch Chrysophycophytes, the class Diatomophyceae and the order Centrales. Diatomophyceae are very widespread in fresh, salt or brackish waters. The life of the species of this class can be planktonic or benthic. The protoplasm is enclosed in a siliceous frustule. The particularly preferred plant is *Skeletonema costatum* (SKC) is a cosmopolitan and usually marine species, which is frequently found to be associated with the phytoplanktonic efflorescences of coastal waters.

The experiments performed by the inventors have made it possible to demonstrate a very surprising enzymatic action of the lipid extracts of this algae. The inventors have demonstrated an inhibitory action on 3',5'-cAMP phosphodiesterase, which has made it possible to envisage its use in cosmetic and pharmaceutical products, especially dermatological products.

3',5'-cAMP phosphodiesterase, hereafter referred to as "phosphodiesterase" or "PDE", is the enzyme which converts cyclic 3',5'-adenosine monophosphate (cAMP), a second messenger involved in the control of cell metabolism, to adenosine monophosphate (AMP), the inactive form of said second messenger. The inhibition of PDE by an inhibitor consequently enables a high intracellular level of cAMP to be maintained, which has the effect especially of activating the protein kinases A and, via this process, makes it possible in particular to promote lipid degradation.

Furthermore, it is also known that cAMP is involved in counteracting certain inflammatory processes (Front Matrix Biol., vol. 6, pp. 193–205, Karger, Busel 1978, Skin inflammatory reactions and cyclic AMP, Georges Cehovic and Nguyen-Ba Giao). It has also been described that PDE increases with age (S. K. Puri and L. Volicer, Mechanisms of Aging en Dev. (1981), 15, 239). The inhibition of PDE will therefore contribute to delaying the appearance of ageing effects, particularly on the skin.

Thus it has been demonstrated by the inventors that, by virtue of their inhibitory action on PDE, the lipid extracts of Skeletonema, particularly the species mentioned above and preferably SKC, are of great value in cosmetics and therapeutics.

In fact, through the discovery of the activity of the lipid extracts of Skeletonema, particularly the species mentioned above and preferably SKC, namely inhibition of the action of PDE, the invention provides different solutions in the fields of cosmetics and therapeutics, especially dermatology.

The inhibition of PDE gives the compositions of the invention a slimming, anti-inflammatory, anti-cellulite and anti-ageing action.

Thus, according to a first feature, the invention relates to a novel lipid extract of the algae Skeletonema, especially an algae selected from the group consisting of *S. tropicum, S. menzehii, S. potamos, S. subsalsum, S. pseudo costatum* and *S. costatum*, and in particular to a total lipid extract of said algae obtained by extraction in an organic solvent.

In one advantageous embodiment of the invention, this lipid extract is characterized in that it is obtained by extracting the algae Skeletonema in an organic solvent which has a polarity index p' of less than about 5.4, preferably of between 2 and 4.5 and particularly preferably of between 4.2 and 4.4, and which is acceptable in the cosmetic or pharmaceutical industry. For the polarity indices of solvents, reference may be made to the article by L. R. SNYDER: Classification of the solvent properties of common liquids; Journal of Chromatography, 92 (1974), 223–230.

In another advantageous embodiment of the invention, the above-mentioned lipid extract is obtained by extracting the algae with an organic solvent selected from the group consisting of isopropanol, ethyl acetate, dichloromethane and chloroformn.

In yet another advantageous embodiment of the invention, the above-mentioned extract is obtained by extracting the algae with isopropanol.

The p' values for each of the above-mentioned solvents are given below by way of example:

isopropanol: 4.3
ethyl acetate: 4.3
chloroform: 4.4
dichloromethane: 3.7

In another advantageous variant, the extraction is performed under reflux.

In another advantageous variant, the algae is frozen before being extracted with the solvent, the freezing preferably being effected at a temperature of between about −40° C. and −20° C. and for a period preferably of between about 1 and 7 days.

In another advantageous variant, the frozen algae is immersed directly in the solvent heated to the reflux temperature. The thermal shock in fact makes it possible to facilitate the decantation of the silica (originating from the skeleton of the algae cells).

In yet another advantageous variant, before any other extraction operation, the algae is macerated in the organic solvent at room temperature, preferably for a period of between about 5 minutes and 80 minutes and particularly preferably for a period of between about 20 minutes and 40 minutes.

In yet another advantageous variant, the amount of organic solvent used is between about 0.1 liter and 20 liters, preferably between about 2 liters and 10 liters, per 100 g of algae, expressed by dry weight of algae.

In yet another advantageous variant, the extraction can be performed under an inert atmosphere, preferably under a nitrogen-saturated atmosphere. This makes it possible in particular to avoid pronounced degradation of the active molecules.

The process can also comprise a simple maceration (only) at room temperature and/or a reflux or a reflux only, at atmospheric pressure, preferably under an inert atmosphere and preferably under a nitrogen-saturated atmosphere.

The amount of organic solvent used is advantageously between about 0.1 liter and 20 liters, preferably between about 2 liters and 10 liters, per 100 g of algae, expressed by dry weight of algae.

The extract will preferably be obtained by a two-step extraction as described below, namely a first solid/liquid extraction step followed by a second fractionation, decolorization and deodorization step.

The extraction can be performed under an inert atmosphere (saturated with nitrogen), making it possible in particular to avoid pronounced degradation of the active molecules.

The extract is advantageously obtained by macerating the algae in a solvent which is preferably acceptable in the cosmetic or pharmaceutical industry and has a polarity index p' of less than about 5.4, preferably of between 2 and 4.5 and particularly preferably of between 4.2 and 4.4.

The extraction will preferably take place under reflux.

The maceration time is preferably between about 5 minutes and about 80 minutes and preferably between about 20 minutes and about 40 minutes.

The whole (biomass+solvent) is refluxed for a period of about 15 minutes to about 2 hours, preferably of between about 20 minutes and about 40 minutes, with agitation (the temperature of the solvent being maintained).

After the reaction mixture has been cooled, the extract is filtered off to separate the extracted biomass from the lipid extract in the solvent.

The lipid extract is then concentrated (the concentration factor being about 71.5).

To start the second step, the lipid extract is taken up in the cold solvent at a rate of about 5 kg to about 15 kg of solvent per kg of oil, preferably at a rate of about 9 kg to about 11 kg of solvent per kg of oil. Agitation is continued for a period of between about 10 minutes and about 60 minutes, preferably of between about 15 minutes and about 25 minutes. The liquor is then filtered to remove the residual sticky sludge.

The decolorization/deodorization treatment is then effected for example with zeolite and active charcoal. The proportion of charcoal can be between about 1% and about 5%, preferably between about 1.5% and about 2%, and the proportion of zeolite can be between about 0.3% and about 4%, preferably between about 0.8% and about 1.2%. The charcoal-to-zeolite ratio can be between about 1 and about 4, preferably between about 1.5 and about 2.

The zeolite and charcoal are then removed, for example by filtration.

Antioxidants can be added to preserve the active molecules, examples being D,L-alpha-tocopherol or one of its esters such as tocopherol phosphate, and/or an ascorbate, particularly an ascorbyl palmitate, preferably at a concentration of between 0.001% and 5% by weight, based on the total weight of said extract. These antioxidants may be incorporated via a stock solution in the extraction solvent.

The filtrate and the antioxidants which may have been added are then concentrated, for example batchwise, to give a brown-colored oil.

This lipid extract is preferably packaged under an inert gas, such as nitrogen, in order to protect the active molecules.

According to a second feature, the present invention further relates to a process for the manufacture of a lipid extract of the algae Skeletonema, in particular a total lipid extract of said algae, characterized in that said algae is extracted with an organic solvent for a sufficient period of time to produce said organic lipid extract. The extraction conditions are as defined in the statement of the first feature of the invention. In particular, the extract is advantageously obtained by extracting the algae Skeletonema in an organic solvent which has a polarity index p' of less than about 5.4, preferably of between 2 and 4.5 and particularly preferably of between 4.2 and 4.4, and which is acceptable in the cosmetic or pharmaceutical industry.

Different variants of the manufacturing process will be clearly apparent to those skilled in the art from the foregoing description relating to the definition of the organic lipid extract within the framework of the first feature.

According to a third feature, the invention relates to a cosmetic composition, characterized in that it comprises, as the active principle, an above-mentioned lipid extract of the above-mentioned algae Skeletonema, in particular a total lipid extract of said algae, in the presence of a cosmetically acceptable vehicle.

Furthermore, as indicated previously, the algae Skeletonema is selected in particular from the group consisting of the algae *Skeletonema tropicum, Skeletonema menzelii, Skeletonema potamos, Skeletonema subsalsum, Skeletonema pseudocostatum* and *Skeletonema costatum*.

In one advantageous embodiment, this composition is characterized in that it is a cosmetic skin care composition containing a cosmetically effective amount of the lipid extract of the above-mentioned algae Skeletonema for combating the effects of skin ageing or inflammatory phenomena.

In another advantageous embodiment, this composition is characterized in that it is a cosmetic skin care composition containing a cosmetically effective amount of the lipid extract of the above-mentioned algae Skeletonema for obtaining a slimming action.

In yet another advantageous embodiment of the invention, this composition is characterized in that it is a cosmetic skin care composition containing a cosmetically effective amount of the lipid extract of the above-mentioned algae Skeletonema for obtaining an anti-cellulite action.

The compositions according to the invention can be formulated in any form acceptable for their use in cosmetology. In particular, a composition can be in a form appropriate for topical application, particularly in the form of a cream or gel and particularly a cream or gel for the face, hands, bust or body.

In yet another advantageous embodiment, this composition comprises from about 0.001% to 10%, particularly from about 0.02% to 1%, by dry weight of said lipid extract, based on the total weight of the final composition.

Other specific characteristics of this cosmetic composition, especially of the extract, are apparent from the foregoing and following description.

In yet another advantageous embodiment, this composition also comprises at least one antioxidant, particularly D,L-$\alpha$-tocopherol or one of its salts or esters such as tocopherol phosphate, and/or an ascorbate, particularly ascorbyl palmitate, preferably at a concentration of between about 0.001% and 5% by weight, based on the total weight of said extract.

According to a fourth feature, the present invention further relates to a pharmaceutical composition, especially dermatological composition, preferably formulated for topical application, characterized in that it comprises, as the active ingredient, an above-mentioned lipid extract of the algae Skeletonema, in particular a total lipid extract of said algae, in a pharmaceutically acceptable vehicle.

In one advantageous embodiment, this composition comprises from about 0.001% to 10%, particularly from about 0.02% to 1%, by dry weight of said lipid extract, based on the total weight of the final composition.

In yet another advantageous embodiment, this composition also comprises at least one antioxidant, particularly D,L-$\alpha$-tocopherol or one of its salts or esters such as tocopherol phosphate, and/or an ascorbate, particularly ascorbyl palmitate, preferably at a concentration of between about 0.001% and 5% by weight, based on the total weight of said extract.

Other specific characteristics of this pharmaceutical composition, especially of the extract, are apparent from the foregoing and following description.

According to a fifth feature, the invention relates to the use of a lipid extract of the algae Skeletonema, in particular a total lipid extract of said algae, as a cosmetic agent, in the presence of a cosmetically acceptable vehicle.

This cosmetic agent will be used especially in any composition with which it is sought in particular to inhibit the action of 3',5'-cAMP phosphodiesterase.

Thus this use is advantageously also characterized in that the above-mentioned extract is an inhibitor of 3',5'-cAMP phosphodiesterase.

In one advantageous embodiment, this use is characterized in that the extract is intended for skin care, in particular for obtaining a slimming action, for combating inflammatory skin phenomena, for delaying or attenuating the effects of skin ageing and for reducing, eliminating or preventing excessive subcutaneous fat deposits, especially cellulite.

This cosmetic agent may therefore be used for combating the effects of skin ageing, especially by preserving or improving the biomechanical qualities of the skin and in particular by improving the firmness or elasticity of the skin, by delaying the appearance of wrinkles or by reducing their depth.

This cosmetic agent may also be used for the care of sensitive skin, especially by attenuating or eliminating the irritative, inflammatory or allergic phenomena which often result in redness or burning or smarting sensations on the skin.

This cosmetic agent may also be used for obtaining a slimming effect on different parts of the body, particularly the hips.

This cosmetic agent is used in particular for combating cellulite.

Thus the cosmetic compositions of the invention will be used especially for any cosmetic applications with which it is sought to inhibit PDE.

As already seen, it has been possible to correlate the efficacy of the above-described cosmetic compositions with an enzymatic activity. Demonstration of this activity has also made it possible to envisage the use of the above-defined lipid extracts for the preparation of pharmaceutical compositions, especially dermatological compositions, in which such an activity is desired. The experiments carried out by the inventors of the present invention have confirmed the efficacy of these pharmaceutical compositions.

Thus the inhibition of PDE results in the maintenance of a high level of intracellular cAMP. This gives rise to a variety of valuable effects on the skin, particularly slimming, anti-ageing, anti-inflammatory and anti-cellulite effects.

According to a sixth feature, the invention further relates to the use of a lipid extract of the algae Skeletonema, in particular a total lipid extract of said algae, as an active principle for the manufacture of a pharmaceutical composition, especially dermatological composition, for obtaining a slimming action, for combating inflammatory skin phenomena and for reducing, eliminating or preventing excessive subcutaneous fat deposits, especially cellulite. Advantageously, this composition will usually comprise said extract incorporated in a pharmaceutically acceptable vehicle.

For these different applications, the pharmaceutical composition advantageously exhibits an inhibitory activity on PDE.

In one variant, the invention relates to the use of a lipid extract of SKC for the preparation of a pharmaceutical composition, especially dermatological composition, for the treatment and prevention of allergic manifestations, particularly skin allergy.

This type of application is directly linked to inhibition of the lipid mediators of inflammation.

In all the applications in the pharmaceutical field, especially dermatological field, the compositions used are preferably compositions for topical application to the skin. Furthermore, the algae lipid extracts used to prepare said compositions are obtained in the same way as the lipid extracts used in the cosmetic field, and are introduced into a pharmaceutically acceptable vehicle, especially dermatologically acceptable vehicle, at concentrations of between about 0.001% and 10%, particularly of between about 0.02% and 1%, by dry weight of said lipid extract, based on the total weight of the final composition.

According to a seventh feature, the present invention relates to a method of cosmetic or pharmaceutical treatment, especially dermatological treatment, characterized in that it comprises the topical application, in particular to the skin of a person in need thereof, of a cosmetically or pharmaceutically effective amount, especially dermatologically effective amount, of a lipid extract of the algae Skeletonema, especially the algae *Skeletonema costatum*, and in particular a total lipid extract of said algae, as defined above, optionally in a cosmetically or pharmaceutically acceptable excipient, especially dermatologically acceptable excipient.

Other characteristics of the method are clearly apparent from the foregoing and following description taken as a whole.

In particular, in one variant, said method is a method of cosmetic slimming treatment comprising the application, to the appropriate skin areas of a person in need thereof, of an effective amount of the above-mentioned lipid extract of the algae Skeletonema for obtaining a slimming effect.

In another variant, said treatment is a cosmetic anti-cellulite treatment comprising the application, to the appropriate skin areas of a person in need thereof, of an effective amount of the above-mentioned lipid extract of the algae Skeletonema for obtaining a cellulite-reducing effect or for delaying the appearance or development of cellulite.

In yet another variant, said treatment is a cosmetic skin anti-ageing treatment comprising the application, to the appropriate skin areas of a person in need thereof, of an effective amount of the above-mentioned lipid extract of the algae Skeletonema for obtaining an anti-ageing effect on said skin areas, especially for improving the firmness or elasticity of the skin, for delaying the appearance of wrinkles or for reducing their depth.

In yet another variant, said treatment is a cosmetic treatment for sensitive skin comprising the application, to the appropriate skin areas of a person in need thereof, of an effective amount of the above-mentioned lipid extract of the algae Skeletonema for attenuating or eliminating the irritative, inflammatory or allergic phenomena which result in redness or burning or smarting sensations on the skin.

This cosmetic treatment can also consist of a skin care treatment for reducing the excessive fat deposits and particularly for combating cellulite.

In the case of a pharmaceutical or therapeutic treatment, said treatment is applied to pathological conditions which clearly result from the foregoing or following description, examples being the treatment and prevention of allergic manifestations, particularly skin allergy.

According to yet another feature, the invention relates to a method of cosmetic or pharmaceutical treatment for maintaining or obtaining a high level of intracellular cAMP in the skin cells, characterized in that it comprises the topical application, to the skin, of a cosmetically or pharmaceutically effective amount of an above-mentioned lipid extract of the algae Skeletonema, especially the algae *Skeletonema costatum*, and in particular a total lipid extract of said algae, for maintaining or obtaining said high level of intracellular cAMP.

In each of the foregoing features, the algae Skeletonema is preferably selected from the group consisting of the algae *Skeletonema tropicum, Skeletonema menzelii, Skeletonema potamos, Skeletonema subsalsum, Skeletonema pseudocostatum* and *Skeletonema costatum*, the algae *Skeletonema costatum* being particularly preferred.

Furthermore, within the framework of a cosmetic or pharmaceutical composition or in the case of a cosmetic or pharmaceutical use, the lipid extract of the algae Skeletonema is a lipid extract obtained with any solvent, i.e. it is not limited to the extracts and the extraction process described and claimed. It is particularly preferred to use a lipid extract of the algae Skeletonema with an organic solvent of low polarity whose index p' is preferably less than about 5.4, preferably between 2 and 4.5 and particularly preferably between 4.2 and 4.4. The specific solvents mentioned above which satisfy these criteria can obviously be used in each of the features of the invention.

Moreover, the preferred embodiment of the invention relates to the use of a lipid extract of the algae *Skeletonema costatum*, preferably a lipid extract of the algae *Skeletonema costatum* as defined above.

Advantageously, the lipid extract of the algae Skeletonema, in particular a total lipid extract of said algae, is obtained from the frozen algae extracted in isopropanol, preferably under reflux.

The Examples which follow are given purely to illustrate the invention.

Other advantages of the invention will become apparent from the description and the Examples which follow.

Unless indicated otherwise, the proportions given in the Examples of compositions are expressed as percentage by weight.

EXAMPLE 1

Preparation of a Lipid Extract According to the Invention

The whole extraction will preferably be performed under an inert atmosphere (nitrogen saturation) in order to avoid pronounced degradation of the active molecules.

250 kg of biomass (*Skeletonema costatum*) are used in this preparation.

The algae, which have been frozen to $-20°$ C., are immersed in IPA (isopropanol) refluxing at 80–83° C., with agitation. The thermal shock makes it possible to facilitate the decantation of the silica (originating from the skeleton of the algae cells).

The amount of solvent used is 10 liters of IPA per liter of water present in the biomass. In this preparation, with a proportion of dry matter of 30%, the 250 kg of biomass represent 75 kg of dry matter and 175 kg of water. The amount of IPA used here is 1925 kg.

The whole (biomass+IPA) is refluxed (i.e. at about 80° C.) for half an hour, with agitation, before being cooled to about 50° C.

After the reaction mixture has been cooled to about 50° C., the extract is transferred to a GUEDU filter in order to separate the extracted biomass from the lipid extract in EPA.

The lipid extract is concentrated in a batch reactor (concentration factor=71.5).

The yield of crude oil in this first step is 28%, based on the dry weight.

To start the second step, the lipid extract is taken up in cold EPA at a rate of 10 kg of solvent per kg of oil. Agitation is continued for 20 minutes. The liquor is then filtered (to remove the residual sticky sludge).

The decolorization and deodorization treatment is carried out in two batches in an 80-liter Schott reactor and takes 30 minutes at room temperature. 0.94 kg of zeolite (ABSENT 2000 supplied by UOP) and 1.6 kg of active charcoal (CXV supplied by CECA) are added, the charcoal-to-zeolite ratio being 1.7.

The zeolite and charcoal are then filtered off on paper.

The yields of this second step is 37%, based on the dry weight.

Thus the overall yield of oil for the whole process is 10%, based on the dry weight of biomass.

Antioxidants (D,L-$\alpha$-tocopherol at a final concentration of 0.05% by weight :and ascorbyl palmitate at a final concentration of 0.05% by weight) are incorporated via a stock solution in IPA.

The filtrate and the antioxidants are then concentrated batchwise to give a brown-colored oil.

This lipid extract is packaged under an inert gas such as nitrogen.

EXAMPLE 2

Demonstration of the Inhibitory Activity of the Lipid Extracts on PDE 2. 1—Principle of the Test for Inhibitory Activity The principle of the test is based on the hydrolysis of cyclic 3'5'-adenosine monophosphate(cAMP) to adenosine monophosphate (AMP). The formation of AMP is measured by HPLC (high performance liquid chromatography) analysis.

The solutions of the reagents are prepared in 0.05 M Tris-HCl buffer at pH 7.5.

The lipid extracts to be tested are at a concentration of 0.1% in DMSO.

The same experiment is carried out with the reference active product theophylline (H. Kather, A. Scheurer, Effects of different phosphodiesterase inhibitors on the antilipolytic action of insulin in human adipocytes: Horm. Metabol. Res. 19 (1987) 379–381). Likewise, B. B. Fredholm, E. Lindger, Acta pharmacol. et toxicol., 54 (1984), pp. 64–71, "The effect of alkylxanthines and other phosphodiesterase inhibitors on adenosine receptor mediated decrease in lipolysis and cyclic AMP accumulation in rat fat cells" . . . These tests are reference tests for those skilled in the art.

The theophylline tested (SIGMA/Ref. T1633) is at a concentration of 0.2% in DMSO.

The composition of the reaction media is described below. The cAMP solution is mixed with the solvent, which may or may not contain the test product and the buffer. PDE, which is in Tris-HCl buffer, is added to this medium immediately before use.

The amount of AMP formed is measured after a reaction time of 5 minutes by calculating the integration area of the AMP peak on the chromatogram produced by the HPLC apparatus (KONTRON S. A.).

The composition of the reaction media is indicated below:

|  | Control sample | Sample with test product |
|---|---|---|
| Substrate (cAMP (WALDHOF/Germany): 0.25% in the buffer) | 80 µl | 80 µl |
| Solvent: DMSO (dimethyl sulfoxide) | 80 µl | 0 |
| Test product (0.1% in DMSO) | 0 | 80 µl |
| Tris-HCl buffer: 0.05 M at pH 7.5 | 480 µl | 480 µl |
| Add immediately before use: | | |
| Enzyme (PDE (SIGMA/Ref. P800): 0.5 U/ml in the buffer) | 160 µl | 160 µl |

2.2—Method of Calculating the Results

The amount of AMP due to the action of PDE is measured after a reaction time of 5 minutes.

This gives an activity "A" of the test product, which is expressed in the form of a percentage inhibition of PDE as defined below:

$$A = \left(\frac{S_t - S_p}{S_t}\right) \times 100$$

where:

$S_t$ is the integration area of AMP for the control sample $S_p$ is the integration area of AMP for the sample with test product

2.3—Results

TABLE I

Inhibition of PDE

| | Integration area of AMP | A (%) | Standard deviation |
|---|---|---|---|
| DMSO | 40.80 | 0 | 0.6 |
| Theophylline | 26.52 | 35 | 2.5 |
| Dry lipid extract of Skeletonema costatum | 23.26 | 43 | 4 |

2.4—Comments on the Results

The results obtained demonstrate the existence of a substantial inhibitory activity of the lipid extract according to the invention on PDE.

This inhibitory activity of the extract according to the invention is at least as substantial as the well-known inhibitory activity of theophylline. It is even possibly greater than that of theophylline.

By virtue of the inhibition of PDE to a very significant extent, the invention makes it possible to maintain a high intracellular level of cAMP, which has the effect especially of activating the protein kinases A and, via this process, makes it possible in particular to promote lipid degradation. The invention therefore affords a slimming action.

Also, given that cAMP is involved in counteracting certain inflammatory processes, the Skeletonema plant extract according to the invention has an anti-inflammatory activity.

The combination of the actions of degrading lipids and limiting inflammatory processes makes it possible to combat cellulite.

Also, given the fact that PDE increases with age, the inhibitory activity on PDE obtained with the extract according to the invention makes it possible to delay the appearance of the signs of ageing. The present experiments clearly demonstrate that the Skeletonema extract according to the present invention can be used in cosmetics or pharmacy for obtaining all the effects described above.

EXAMPLE 3

| Cream for sensitive skin | |
|---|---|
| Fluid mineral oil | 7.50 g |
| Octyl octanoate | 5.00 g |
| Cetostearyl octanoate | 5.00 g |
| Methyl glucose sesquistearate | 3.00 g |
| Beeswax | 3.00 g |
| Glycerol | 3.00 g |
| Xanthan gum | 0.50 g |
| Perfume | 0.30 g |
| Phenoxyethanol | 0.20 g |
| Dry lipid extract of Skeletonema costatum | 0.05 g |
| Color | qs g |
| Water | qsp 100.00 g |

EXAMPLE 4

| Soothing lotion | |
|---|---|
| Hannarelis floral water | 5.00 g |
| Methyl glucose POE 20 | 2.00 g |
| Glycerol | 2.00 g |
| Polysorbate 20 | 1.50 g |
| Methyl parahydroxybenzoate | 0.15 g |
| Tetrasodium EDTA | 0.10 g |
| Perfume | 0.10 g |
| Dry lipid extract of Skeletonema costatum | 0.05 g |
| Color | qs g |
| Citric acid/sodium citrate | qsp (pH = 6.50) g |
| Water | qsp 100 g |

EXAMPLE 5

| Aqueous-alcoholic slimmin gel | |
|---|---|
| Denatured alcohol (ethanol) | 30.00 g |
| Glycerol | 2.00 g |
| Carbomer | 0.50 g |
| Triethanolamine | 0.50 g |
| Dry lipid extract of Skeletonema costatum | 0.10 g |
| Water | qsp 100.00 g |

What is claimed is:

1. A method of cosmetic care selected from the group consisting of a slimming care, a cellulite-reducing care and a care delaying the appearance or development of cellulite, comprising applying to skin areas of a person in need thereof, a cosmetically effective amount for said care of a lipid extract of the algae Skeletonema obtained by extraction in an organic solvent.

2. The method of claim 1, wherein the algae Skeletonema is selected from the group consisting of *S. tropicum, S. menzelii, S. potamos, S. subsalsum, S. pseudocostatum* and *S. costatum*.

3. The method of claim 1, wherein said lipid extract is obtained by extracting the algae Skeletonema in an organic solvent which has a polarity index p' of less than about 5.4, and which is acceptable in the cosmetic industry.

4. The method of claim 1, wherein the extract is obtained by extracting the algae with an organic solvent selected from the group consisting of isopropanol, ethyl acetate, dichloromethane and chloroform.

5. The method of claim 1, wherein the extract is obtained by extracting the algae with isopropanol.

6. The method of claim 1, wherein the extraction is performed under reflux.

7. The method of claim 1, wherein the algae is frozen at a temperature of between about −40° C. and −20° C. for a period of between about 1 and 7 days, and the frozen algae is extracted with the solvent.

8. The method of claim 7, wherein the frozen algae is immersed directly in the solvent heated to a reflux temperature of between about 80° C. to about 83° C.

9. The method of claim 1, wherein, before extraction, the algae is macerated in the solvent at room temperature.

10. The method of claim 1, wherein the amount of solvent is between about 0.1 liter and 20 liters, per 100 g of algae, expressed by dry weight of algae.

11. The method of claim 1, wherein the extraction is performed under an inert atmosphere.

12. The method of claim 1 comprising applying on said skin areas a cosmetic composition comprising from about 0.001% to 10% by dry weight of said lipid extract, based on the total weight of the cosmetic composition.

13. The method of claim 1, comprising applying to said skin areas a cosmetic composition comprising from about 0.02% to 1% by dry weight of said lipid extract, based on the total weight of the cosmetic composition.

14. The method of claim 1, comprising applying to said skin areas a cosmetic composition comprising said lipid extract and at least one antioxidant.

15. The method of claim 14, wherein the concentration of said antioxidant is ranging between about 0.001% and 5% by weight, based on the total weight of said extract.

16. The method of claim 14, wherein said antioxidant is selected from the group consisting of a tocopherol, tocopherol phosphate, an ascorbate and ascorbyl palmitate.

17. A method of skin care for obtaining a slimming action on skin areas in need thereof, for reducing, eliminating or delaying formation of excessive sub-cutaneous fat deposits, comprising applying to said skin areas in need thereof of a cosmetically effective amount of a lipid extract of the algae *Skeletonema costatum* obtained by extracting the algae in a frozen form in isopropanol.

18. The method of claim 17, comprising applying to said skin areas a cosmetic composition comprising from 0.001% to 10% by dry weight of said lipid extract based on the total weight of the cosmetic composition.

19. The method of claim 18, wherein said cosmetic composition further comprises at least one antioxidant.

20. The method of claim 19, wherein said antioxidant is present in said cosmetic composition at a concentration ranging between about 0.001% and 5% by weight, based on the total weight of said extract.

21. The method of claim 3, wherein said lipid extract has a polarity index p' of between 2 and 4.5.

22. A method of cosmetic care selected from the group consisting of a slimming care, a cellulite-reducing care and a care delaying the appearance or development of cellulite, comprising applying to skin areas of a person in need thereof, a cosmetically effective amount for said care of a lipid extract of the algae Skeletonema obtained by extraction in an organic solvent, wherein the algae Skeletonema is selected from the group consisting of *S. tropicum, S. menzelii, S. potamos, S. subsalsum, S. pseudocostatum* and *S. costaturn*.

23. A method of cosmetic care selected from the group consisting of a slimming care, a cellulite-reducing care and a care delaying the appearance or development of cellulite, comprising applying to skin areas of a person in need thereof, a cosmetically effective amount for said care of a lipid extract of the algae Skeletonema obtained by extraction in an organic solvent, wherein the extract is obtained by extracting the algae with an organic solvent selected from the group consisting of isopropanol, ethyl acetate, dichloromethane and chloroform.

24. A method of cosmetic care selected from the group consisting of a slimming care, a cellulite-reducing care and a care delaying the appearance or development of cellulite, comprising applying to skin areas of a person in need thereof, a cosmetically effective amount for said care of a lipid extract of the algae Skeletonema obtained by extraction in an organic solvent, wherein the extract is obtained by extracting the algae with an organic solvent selected from the group consisting of isopropanol, ethyl acetate, dichloromethane and chloroform, and wherein the algae is frozen at a temperature of between about −40° C. and −20° C. for a period of between about 1 and 7 days before being extracted with the solvent.

* * * * *

UNITED STATES PATENT AND TRADEMARK OFFICE
CERTIFICATE OF CORRECTION

PATENT NO. : 6,447,782 B1
DATED : September 10, 2002
INVENTOR(S) : Viron et al.

It is certified that error appears in the above-identified patent and that said Letters Patent is hereby corrected as shown below:

Column 12,
Line 22, after "S." and before "." please replace "*costaturn*" with -- *costatum* --.

Signed and Sealed this

Fourth Day of February, 2003

JAMES E. ROGAN
*Director of the United States Patent and Trademark Office*